US00RE46705E

(19) United States
(12) Reissued Patent
Figulla et al.

(10) Patent Number: US RE46,705 E
(45) Date of Reissued Patent: Feb. 13, 2018

(54) OCCLUSION DEVICE FOR OCCLUDING AN ATRIAL AURICULA AND METHOD FOR PRODUCING SAME

(71) Applicant: Occlutech Holding AG, Schaffhausen (CH)

(72) Inventors: Hans Reiner Figulla, Jena (DE); Friedrich Moszner, Hohlstedt (DE); Robert Moszner, Bad Klosterlausnitz (DE); Rüdiger Ottma, Grossschwabhausen (DE); Christopf Damm, Jena (DE); Susann Klebon, Jena (DE)

(73) Assignee: Occlutech Holding AG, Schaffhausen (CH)

(21) Appl. No.: 14/164,101

(22) Filed: Jan. 24, 2014

Related U.S. Patent Documents

Reissue of:
(64) Patent No.: 8,100,938
Issued: Jan. 24, 2012
Appl. No.: 11/271,751
Filed: Nov. 14, 2005

(51) Int. Cl.
*A61D 1/00* (2006.01)
*A61B 17/00* (2006.01)

(52) U.S. Cl.
CPC ..... *A61B 17/0057* (2013.01)

(58) Field of Classification Search
CPC ..... A61B 17/0075; A61B 17/12022; A61B 17/12122; A61B 17/12172; A61B 2017/00575
USPC ..... 604/107, 96.01, 101.05, 164.13, 103.07, 604/509, 500, 264, 28, 528, 536; 128/830, 887; 606/7, 15, 213, 108, 194, 606/159, 185, 200, 139, 144, 148
See application file for complete search history.

(56) References Cited

U.S. PATENT DOCUMENTS 5,725,552 A * 3/1998 Kotula et al. ..... 606/213
6,174,322 B1 * 1/2001 Schneidt ..... 606/213
(Continued)

FOREIGN PATENT DOCUMENTS

WO WO 2005099365 A2 * 10/2005

OTHER PUBLICATIONS

United States Patent and Trademark Office, Notice of Allowance dated Oct. 3, 2011 in U.S. Appl. No. 11/271,751, 9 pages.
(Continued)

*Primary Examiner* — Julie A Szpira
(74) *Attorney, Agent, or Firm* — Inskeep IP Group, Inc.

(57) ABSTRACT

A self-expanding occlusion device for occluding an atrial auricula in the heart of a patient includes a braiding of thin wires or threads given a suitable profile form by means of a molding and heat treatment procedure. The occlusion device includes a proximal retention area, a distal retention area and a center section. The occlusion device holds securely in the atrial auricula of a patient in its expanded and implanted state without damaging the tissue of the patient's heart. The proximal retention area has a flanged area which positions at the inner walls of the atrial auricula when the occlusion device is in an expanded state in the atrial auricula to be occluded, and forms a force-fit connection with the inner walls of the atrial auricula, thus holding the implanted and expanded occlusion device in the atrial auricula, whereby the distal retention area closes the opening in the atrial auricula.

42 Claims, 4 Drawing Sheets

(56) References Cited

U.S. PATENT DOCUMENTS

| | | | | |
|---|---|---|---|---|
| 6,334,864 | B1 | 1/2002 | Amplatz et al. | |
| 2005/0004652 | A1* | 1/2005 | van der Burg et al. | 623/1.12 |
| 2006/0247680 | A1* | 11/2006 | Amplatz et al. | 606/213 |

OTHER PUBLICATIONS

United States Patent and Trademark Office, Final Office Action dated Apr. 28, 2010 in U.S. Appl. No. 11/271,751, 12 pages.
United States Patent and Trademark Office, Examiner Interview Summary dated Dec. 2, 2009 in U.S. Appl. No. 11/271,751, 3 pages.
United States Patent and Trademark Office, Office Action dated Jun. 10, 2009 in U.S. Appl. No. 11/271,751, 14 pages.
United States Patent and Trademark Office, Final Office Action dated Jan. 9, 2009 in U.S. Appl. No. 11/271,751, 14 pages.
United States Patent and Trademark Office, Office Action and Examiner Interview Summary dated Feb. 25, 2008 in U.S. Appl. No. 11/271,751, 16 pages.

* cited by examiner

OCCLUSION DEVICE FOR OCCLUDING AN ATRIAL AURICULA AND METHOD FOR PRODUCING SAME

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND OF THE INVENTION

1. Field of the Invention

The present invention relates to a self-expanding occlusion device for occluding an atrial auricula including a braiding of thin wires or threads given a suitable form by means of a molding and heat treatment procedure, whereby the occlusion device has a rear proximal retention area and a front distal retention area and whereby the ends of the wires or threads converge in a holder in the distal retention area. The occlusion device moreover has a center section between the proximal and the distal retention area.

The occlusion device is configured in such a manner that it can be introduced into the body of a patient in collapsed state and positioned in the atrial auricula of the patient in a minimally invasive procedure using a catheter. The invention furthermore relates to a method for the production of such an occlusion device.

2. Description of the Related Art

The principle behind this type of occlusion device is known to at least some extent in medical technology. For example, an occlusion device for treating septum defects is known from DE 10 338 702 of Aug. 22, 2003, consisting of a braiding of thin wires or threads and given a suitable profile in a molding and heat treatment process. The known occlusion device has a proximal retention area which is particularly distinctly flat, a distal retention area, and a cylindrical crosspiece between the proximal and distal retention areas. The ends of the wires forming the braiding converge into a holder in the distal retention area. This structural design thus allows the two retention areas of the known occlusion device to position on the two sides of a shunt to be occluded in a septum, usually by means of an intravascular surgical procedure, while the cross-piece transverses the shunt.

Medical technology has long endeavored to be able to occlude septal defects, for instance atrioseptal defects, by means of non-surgical transvenous catheter procedures, in other words, without having to perform an operation in the literal sense. Various different occlusion systems have been proposed to this end, each with their own pros and cons, without any one specific occlusion system having yet become widely accepted.

In making reference to these different systems, the following will use the terms "occluder" or "occlusion device." In all interventional occlusion systems, a self-expanding umbrella system is introduced transvenously into a defect to be occluded in a septum. This type of system might include two umbrellas: one, for example, positioned at the distal side of the septum (i.e. the side furthest from the median plane of the body/heart) and one at the proximal side of the septum (i.e. the side closer to the median plane of the body), whereby the two umbrella prostheses are subsequently secured to a double umbrella in the septal defect. Thus, in the assembled state, the occlusion system usually consists of two clamped umbrellas connected to one another by means of a short bolt transversing the defect.

However, a disadvantage to such prior art occlusion devices turns out to be the relatively complicated, difficult and complex implantation procedure. Apart from the complicated implantation of the occlusion system in the septal defect to be occluded, the umbrellas utilized are susceptible to material fatigue along with fragment fracture. Furthermore, thromboembolic complications are frequently to be anticipated.

In order to enable the inventive occlusion device to be introduced by means of a surgical insertion instrument and/or guidewire, a holder is provided at the end of the distal retention area for engaging with the insertion instrument and/or guidewire. It is thereby intended that this engagement can be readily disengaged after positioning the occlusion device in the defect. For example, it is possible to devise the braiding at the end of the distal retention area of the occlusion device in such a manner so as to create an internal threading in the holder to engage with the insertion instrument. Of course, other embodiments are naturally also conceivable.

With another type of occlusion device, the so-called Lock-Clamshell umbrella system, two stainless steel preferably Dacron-covered umbrellas are provided, each stabilized by four arms. This type of occluder is implanted into the patient through a vein. However, seen as problematic with the Lock-Clamshell occluder is the fact that the insertion instruments necessary to implant the device need to be of relatively large size. A further disadvantage seen with other systems, for example the Amplatz occluder, is that many different occluder sizes are needed in order to cope with the respective dimensions of the septal defects to be occluded. It thus turns out that the umbrellas do not flatten out completely in the inserted state if the length or the diameter of the crosspiece inserted into the defect is not of an optimum match. This results in incomplete endothelialization. It has furthermore been shown that many of the systems implanted into patients' bodies exhibit material fatigue and fractures in the metallic structures due to the substantial mechanical stresses over a longer period. This is especially the case given permanent stress between an implant and the septum.

In order to overcome these disadvantages, self-centering occlusion devices have been developed which are inserted into the body of the patient and introduced into the septal defect to be occluded by way of a minimally invasive procedure, for example using a catheter and guidewires. Their design is based on the principle that the occlusion device can be tapered to the dimensions of the insertion instrument/catheter used for the intravascular procedure. Such a tapered occlusion device is then introduced by catheter into the septal defect to be occluded, respectively into the shunt of the septum defect to be occluded. The occluder is then discharged from the catheter, upon which the self-expanding umbrellas, retention plates respectively, subsequently unfold against the two sides of the septum. The umbrellas in turn comprise fabric inserts made from or covered by, for example, Dacron, with which the defect/shunt is occluded. The implants remaining in the body are more or less completely ingrown by the body's own tissue after a few weeks or months.

An example of a self-centering occlusion device of the type specified is known from WO 99/12478 A1, which is a further development of the occlusion device known as the "Amplatz occluder" in accordance with U.S. Pat. No. 5,725,552. Same consists of a braiding of a plurality of fine, intertwined nitinol wire strands in the shape of a yo-yo. Each braiding is produced in its original form as a rounded braiding having loose wire ends both at its leading end (its proximal side, respectively) as well as at its trailing end (its distal side, respectively). During the subsequent processing of the rounded braiding, each of these loose ends must then be bundled into a sleeve and welded together. After the appropriate processing, both the proximal as well as the distal side of the finished occluder exhibit a protruding collar. Dacron patches are sewn into the distal and proximal retention umbrellas and the interposed crosspiece. Because of the memory effect exhibited by the nitinol material used, the two retention umbrellas unfold by themselves upon exiting the catheter, initially in a balloon-like intermediate stage, whereby the retention umbrellas ultimately positioned on the two sides of the septum eventually assume a more or less flattened form. The crosspiece centers itself automatically into the shunt to be occluded as the umbrellas unfold.

Yet embolic-related problems can arise with an inserted implant due to the protruding collar at the proximal retention area of the occluder, consecutive embolization in particular. Such embolic-related problems arise in particular in cases of patients suffering from so-called atrial fibrillation. Atrial fibrillation is a condition in which the atria of the heart experiences frequent electrical discharge, leading to the atria not contracting. One consequence of this lack of contraction to the atria of the heart is that there is no effective delivery or mixing of the blood and thrombi can form in the atrium. A considerable risk of thrombi developing in an atrium in consequence of atrial fibrillation is that such thrombi can be carried along in the bloodstream and enter the arterial circulation. Strokes are an especially frequent consequence of such embolization, occurring at a rate of roughly 5% per year in patients with atrial fibrillation when not treated chronically with so-called dicumerol to inhibit blood clots. However, effecting the inhibition of blood clots with so-called dicumerol is likewise not without risk. Since the side effects of dicumerol treatment include increased bleeding, contraindications for this treatment arise for approximately 20% of all patients with atrial fibrillation and patients also have to come to terms with the risk of stroke when weighing the hemorrhage/stroke risks.

In the great majority of cases, thrombi forming in the atrium of the heart develop in the so-called atrial auricula. The atrial auricula are appendages found in the atrium of the human heart. The right atrial auricula is situated near the aorta ascendens, the left near the large pulmonary artery. Blood clots which could potentially lead to strokes develop most frequently in the left atrial auricula in patients with atrial fibrillation.

Because of the risks and problems cited in connection with the above-described formation of thrombi in the atrial auricula, the task facing the present invention is that of providing an occlusion device which can be used to occlude the atrial auricula of the left atrium in order to significantly reduce the formation of thrombi coupled with the risk of stroke. To be provided in particular is an occlusion device with which the risk of stroke is also reduced for those patients for whom inhibiting blood clots with dicumerol (so-called anticoagulation) is contraindicated due to bleeding tendencies.

SUMMARY OF THE INVENTION

This task is solved with a self-expanding occlusion device for occluding an atrial auricula, whereby said occlusion device includes a braiding of thin wires or threads given a suitable form in a molding and heat treatment procedure. It is provided for the occlusion device to have a rear proximal retention area and a front distal retention area as well as a center section arranged between said proximal and said distal retention areas, whereby the ends of the wires or threads converge into a holder in the distal retention area and whereby the occlusion device can be introduced in collapsed state into the body of a patient and positioned in the atrial auricula of the patient in a minimally invasive procedure using a catheter. It is thereby provided in accordance with invention for the proximal retention area to have a flanged area which positions at the inner walls of the atrial auricula when the occlusion device is in expanded state in the atrial auricula to be occluded, forming a force-fit connection with the inner walls of the atrial auricula in order to hold the implanted and expanded occlusion device in the atrial auricula by the distal retention area of the occlusion device closing the opening in the atrial auricula.

The inventive solution has a number of substantial advantages over the occlusion devices known from the prior art as described above. Firstly, the inventive occluder is a self-expanding device which is especially easy to implant, for example with the appropriate insertion catheter. A procedure indicated as an example would be puncturing a vein in the patient's groin area and guiding the insertion catheter system through to the septum of the right atrium. The left atrium of the heart can be reached by puncturing the septum of the atrium, for example by a known transseptal puncture, so that the insertion catheter system can subsequently be introduced from the groin vein into the left atrial auricula. The self-expanding occlusion device for occluding the atrial auricula can then be introduced by the insertion catheter system.

The occlusion device, which remains in collapsed state during the implantation, preferably has a diameter of from 6 to 10 French so that the surgical procedure for occluding the atrial auricula is minimally invasive.

After the collapsed occlusion device has been positioned in the atrial auricula to be occluded using, for example, an insertion catheter, the occlusion device is released from the catheter, upon which it unfolds in response to its self-expanding nature and assumes its distinctive shape induced by the molding and heat treatment procedure used during its manufacture. In this expanded state, the rear proximal retention area with the flanged area configured thereupon is unfolded completely and positions against the inner walls of the atrial auricula to be occluded. In so doing, the proximal retention area with the flanged area configured thereupon serves in the fixing and positioning of the expanded occlusion device in the atrial auricula. The center section extending toward the opening in the atrial auricula from the proximal retention area as well as the distal retention area provided at the distal end of the center section thereby fill the open area of the atrial auricula virtually in complete fashion so that the entire expanded occlusion device in inserted state serves as a plug in occluding the atrial auricula. The formation of thrombi coupled with the risk of stroke can thus be considerably reduced in an especially simple and minimally invasive way.

Especially because the positioning and fixing of the occlusion device makes use of the flanged area which positions at the inner walls of the atrial auricula, the occlusion device can dispense with the fastening hooks or other anchoring means as normally used with such occlusion devices for fixing and positioning the device in the tissue. Of particular consideration in this respect is that because the tissue walls near the atrial auricula are extremely thin, conventionally-used fastening hooks cannot provide a permanent fixing and positioning for the occlusion device. The inventive solution and especially the flanged area disposed on the proximal retention area can circumvent the problems associated with fixing the occlusion device to the extremely thin-walled and easily-lacerated tissue of the atrial auricula when using hooks.

It is thus preferably provided for the occlusion device to have its proximal retention area with the flanged area be configured such that this area distends outward upon expanding of the occlusion device so as to thus position against the inner walls of the atrial auricula in the inserted state. This embodiment enables an insertion catheter system to be able to urge the inventive self-expanding occlusion device particularly deep into the atrial auricula to be occluded. The distal retention area, which is configured in particularly advantageous manner as a distal umbrella, unfolds and positions thereafter; i.e., after the catheter system has inserted the occlusion device into the atrial auricula to be occluded, whereby the umbrella abuts against the edge of the atrial auricula opening at the entrance to the atrial auricula. At the same time, the proximal area of the occlusion device; i.e., the proximal umbrella, expands and in the process of expanding, the proximal umbrella of the occlusion device's proximal retention area is pulled farther into the atrial auricula and a tractive force is thus exerted on the distal umbrella across the center section. As a direct consequence thereof, the distal umbrella, the distal retention area respectively, is held by imposed permanent stress at the opening to the atrial auricula. In other words, the advantageous embodiment of the self-expanding occlusion device provides a self-positioning and self-retaining occlusion device, whereby the position held by the distal umbrella is preferably flush with the opening of the atrial auricula by means of the proximal umbrella distending outwardly by itself.

Another embodiment furthermore provides for the proximal retention area of the occlusion device to exhibit a shape which flares toward the proximal end. What this thereby realizes in particularly advantageous manner is that the occlusion device automatically fits to the inner wall of the atrial auricula—independent of the relative diameter of the atrial auricula to be occluded and independent of the thickness to the atrial auricula wall—which, in particular, ensures a secure hold of the expanded occlusion device in the atrial auricula. Configuring the occlusion device as a fabric and due to the proximal retention area's tapered shape to the proximal end further enables the implanted occlusion device to independently partake in certain independent movements of the atrial auricula; this plays a considerable role, above all as regards material fatigue and the long-lasting and reliable functioning of the occlusion device—in particular, precluding the usual complications which normally arise in such cases.

The flexible and yet at the same time force-fit positioning of the flanged area at the inner wall of the atrial auricula moreover enables the inserted occlusion device to be fully ingrown by the body's own tissue considerably faster than is the case with the known prior art occluding systems.

Further advantages can yield from using a braiding made of thin wires or threads as the starting material for the inventive occlusion device in that same exhibits long-term mechanical stability. As already indicated, structural fractures or other types of material fatigue can be largely prevented in the inserted implant. Such a braiding moreover has sufficient rigidity.

The flanged area configured at the proximal end together with the tapered profile to the proximal retention area of the braiding additionally allows the proximal retention area of the occlusion device to unfold completely at the inner walls of the atrial auricula in the inserted and expanded state, and to do so virtually independent of the diameter to the hole in the atrial auricula or the thickness of the atrial auricula's inner walls. Because a holder on the proximal retention area for bundling or gathering the braiding together can be dispensed with, no components of the occlusion device protrude any farther into the atrial auricula so that neither is there any threat of the body mounting defense mechanism reactions or of there being any other conceivable complications.

A particularly advantageous embodiment of the inventive occlusion device provides for the flanged area configured at the proximal retention to be flared toward the distal end by folding back of the proximal retention area. This is an especially easy realized and thereby effective way to configure the flanged area for the occlusion device. In particular, it is thus possible to form the entire occlusion device from one integral braiding such that, on the one hand, no mechanic connective element will be needed between the flanged area and the proximal end and, on the other, the dimensions to the occlusion device in its collapsed state can be even further reduced. Other embodiments for configuring the flanged area at the proximal retention area are, of course, also conceivable.

In order to have the distal retention area of the occlusion device flatten fully in the implanted and expanded state at the lateral edge of the atrial auricula hole, and to do so virtually independently of the diameter to said atrial auricula hole, a particularly advantageous development of the above-mentioned embodiment of the occlusion device provides for the distal retention area to be provided with a recess in which the holder is disposed. By arranging the holder in the recess provided at the distal end of the occlusion device, no components of the occlusion device protrude beyond the atrial auricula wall, thus preventing components of the implant from being in constant contact with the blood. This yields the advantage of there being no threat that the body will mount defense mechanism reactions or of there being thrombembolic complications. Especially because the expanded occlusion device expands, positions and fixes itself in the opening of the atrial auricula, whereby the distal and proximal retention areas are radially pre-stressed, the occlusion device can be used for a wide range of atrial auricula openings of various different sizes.

A particular development of the latter embodiment of the inventive occlusion device in which the distal retention area exhibits a recess further provides for the distal end of the occlusion device to further exhibit a connective element in the recess, whereby said connective element can engage with a catheter. This connective element, which is arranged on the occlusion device such that it does not protrude beyond the atrial auricula wall, thereby preventing components of the implant from coming into constant contact with the blood, further provides the inventive occlusion device with the functionality of retrievability. In addition, a connective element which can engage with a catheter facilitates implantation and positioning of the occlusion device (collapsed during the implanting procedure) in the atrial auricula to be occluded. Various devices are conceivable as connective elements. For example, latching members or even hooks/eyelets which force-lock with the correspondingly configured complementary connective elements of a catheter would be feasible.

Another advantageous embodiment provides for the occlusion device to be configured so as to be reversibly collapsible inward and outward so that the device can be collapsed in its expanded state, for example with the help of an explantation catheter in the disengaging of the force-fit connection between the flanged area configured on the proximal retention area and the inner wall of the atrial auricula. In conjunction hereto, it is conceivable for a catheter in the explantation procedure to, for example, engage with connective elements configured at the distal end of the occlusion device and to have the collapsing of the occlusion device be occasioned in response to external manipulation of the catheter. The occlusion device is thereby fully reversibly retractable in the catheter, enabling the complete removal of the device.

In order to ensure that the braiding of the occlusion device will maintain the shape it was given by means of its molding and heat treatment procedure, a particularly preferable embodiment provides for the braiding to be made from a shape memory material, in particular nitinol or a polymer synthetic. Using nitinol for occluders is known. Shape-memory polymers are included in the group known as smart polymers and are polymers which exhibit a shape memory effect; i.e., which are able to change their external form in response to external stimuli such as, for example, a change in temperature.

To this end, the polymer is first given its permanent shape using conventional processing methods such as injection molding or extrusion. The synthetic is then subsequently deformed and fixed in its desired temporary shape, a process known as "programming." In the case of polymers, this process can ensue by heating, deforming and then cooling a specimen. Or the polymer/synthetic can also be deformed at lower temperature, a process known as "cold drawing." The permanent shape thus becomes a remembered memory shape while still in its current temporary shape. Should the molded polymer body now be heated to a temperature which is higher than the switching temperature, this leads to a triggering of the shape memory effect and thus to a restoring of the permanent memory shape. Cooling the specimen effects an irreversible degeneration of the temporary shape, which is why this is referred to as a so-called one-way shape memory effect.

Shape memory polymers are far superior in terms of memory properties than the known shape memory materials such as, for example, the nitinol shape memory alloy, an atomistic alloy of nickel and titanium. Only little effort is required from the (heating/cooling) process to program the temporary shape or, respectively, to restore the permanent shape. Moreover, in the case of nitinol, for example, the maximum deformation between permanent and temporary form amounts to just 8%. In contrast, shape memory polymers exhibit substantially higher deformability capabilities of up to 1100%. In accordance with the present invention, all afore-mentioned shape memory polymers are claimed for biomedical application of the occlusion device as specified at the outset.

An advantageous development of the latter above-described embodiment of the inventive occlusion device in which the braiding is made from a shape memory material provides for the material to be a biologically degradable shape memory polymer material. Synthetic, biodegradable implant materials are particularly well-suited hereto. Such types of degradable materials or polymers have bonds which are fissionable under physiological conditions. "Degradableness" is the term used if a material decomposes from loss of mechanical properties due to or within a biological system. An implant's external form and dimensions may in fact remain intact during the decomposition. What is meant with respect to degradation time, provided no additional quantifying data is given, is the time it takes for the complete loss of mechanical properties. Biostable materials refer to materials which remain stable within biological systems and which degrade at least only partially over the long term.

In terms of degradable polymers, a distinction is made between hydrolytically and enzymatically degradable polymers. Hydrolytic degradation has the advantage that the rate at which degradation occurs is independent of the implant site since water is present throughout the system. Given biodegradable polymers or materials, degradation can thus occur through pure hydrolysis, enzymatically-induced reactions or through a combination thereof. Typical hydrolyzable chemical bonds are amide, ester or acetal bonds. Two mechanisms can be noted with respect to the actual degradation. With surface degradation, the hydrolysis of chemical bonds transpires exclusively at the surface. Because of the hydrophobic character, polymer degradation is faster than the water diffusion within the material. This mechanism is seen especially with poly(anhydrides) and poly(orthoesters). As relates to the poly(hydroxy carboxylic acids) particularly significant especially to the shape memory effect such as poly(lactic acid) or poly(glycol acid), the corresponding copolymers respectively, polymer degradation transpires throughout the entire volume. The step which determines the rate here is the hydrolytic fission of the bonds since water diffusion in the somewhat hydrophilic polymer matrix occurs at a relatively fast rate. Decisive for the use of biodegradable polymers is that, on the one hand, they degrade at a controlled or variable speed and, on the other, that the products of decomposition are non-toxic.

In terms of the shape to the inventive occlusion device, it is particularly preferred for the occlusion device to exhibit a bell-shaped profile, whereby the tapered end of this bell-shaped contouring forms the distal retention area. Alternatively, the occlusion device can also exhibit a mushroom-shaped profile, whereby the cap of this mushroom shape forms the proximal or distal retention area. It is additionally conceivable for the occlusion device to exhibit a barbell-shaped profile, whereby the center segment of this barbell shape forms the center section between the proximal and the distal retention area of the occlusion device. Of course, other contourings, as chosen on the basis of the intended application, would be just as conceivable.

It is particularly preferred for the braiding of the inventive occlusion device to be tapered to the diameter of a catheter to be used in a minimally invasive surgical procedure. The advantage to this embodiment can be seen in that it allows the catheter system used in the implantation and explantation to have a considerably smaller internal diameter, which substantially increases the maneuverability of the occlusion device to be implanted and thus improves the positioning accuracy of the device in the atrial auricula. In the case of an occluder made from nitinol, the internal diameter of a catheter used for its implantation or explantation will measure between 8 and 10 French whereas when using occlusion devices made from a synthetic polymer, the internal diameter need only be between 6 and 8 French.

Last but not least, it is particularly preferred for the occlusion device to have at least one fabric insert arranged in or on the distal retention area or in the center section of the occlusion device so as to completely occlude the atrial auricula. This fabric insert serves in closing the gaps remaining in the center area and in the expanding diameters of the occlusion device following insertion and expanding of the device in the atrial auricula. For example, the fabric insert is affixed to the braiding at the distal retention area in such a manner that it can be stretched over the distal retention area like a cloth. The advantage to this design lies in the fact that the lateral edge of the distal retention area is flush with the opening in the atrial auricula and less foreign material is introduced into the body of the patient. The fabric inserts can be made of Dacron, for example. Of course, other materials and other positionings to the fabric insert in or on the occlusion device are also feasible here.

The inventive procedure affords the prospect of realizing a particularly simple manufacturing of the occlusion device described above. First, a funnel-shaped hollow braiding is formed, for example using a round braiding machine. The technology used here can be one in which the configured braiding is bundled at the end of the length of the braiding; i.e., at what will later be the distal end of the occlusion device, while the start of the length of the braiding; i.e., what will later be the proximal end of the occlusion device, remains open. It is thereby possible to produce a funnel-shaped hollow braiding, the bundled end of which corresponds to the distal end of the finished occlusion device and the opposite open end to the proximal end of the finished occlusion device. Because a known braiding procedure can be used to produce the occlusion device, the occlusion device produced exhibits mechanical properties in terms of, for example, expansion, stability, strength, etc., which can be individually adapted to the later use of the occlusion device. In advantageous manner, metallic wires or even organic threads can be worked into the braiding.

With respect to the method, it is preferably provided for the process step of forming the retention areas and the center section to include a procedural step of molding and/or heat treatment. This is of particular advantage when the configured, funnel-shaped hollow braiding is made of nitinol or of another material, especially polymer, which has shape memory properties or effect. Preferably provided for the inventive occlusion device is forming the braiding from a shape memory polymer which is based, for example, on a polyanhydride matrix or on polyhydroxycarboxylic acids. These are synthetic, biodegradable materials which have a thermally-induced shape memory effect. Yet also conceivable would be other shape memory polymers such as, for example, block copolymers as described e.g. in the special edition of Angewandte Chemie[1] 2002 114 by A. Lendlein and S. Kelch, pages 2138 to 2162. It is a simple matter to bring such materials into the applicable final form using a combination of molding and heat treatment procedural steps. A final formed occluder can then be tapered to the dimensions of a catheter, for example. After exiting the catheter, the occlusion device then unfolds by itself and again assumes that shape to the funnel-shaped hollow braiding to which the occlusion device was molded during the manufacturing process by means of the molding and heat treatment step.

[1] Applied Chemistry

It is preferred for the funnel-shaped hollow braiding to be manufactured in such a manner that the thin wires or threads constituting the finished braiding intertwine at the proximal end of said braiding when forming the funnel-shaped hollow braiding. This represents a conceivable and readily realizable manner of producing an occlusion device in accordance with the present invention, the proximal retention area of which exhibits a form flared to the proximal end. Of course, other manufacturing methods are naturally also conceivable.

There has thus been outlined, rather broadly, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

The following will make reference to the drawings in providing a more precise detailing of preferred embodiments of the inventive occlusion device.

DESCRIPTION OF THE INVENTION

Figure 1:
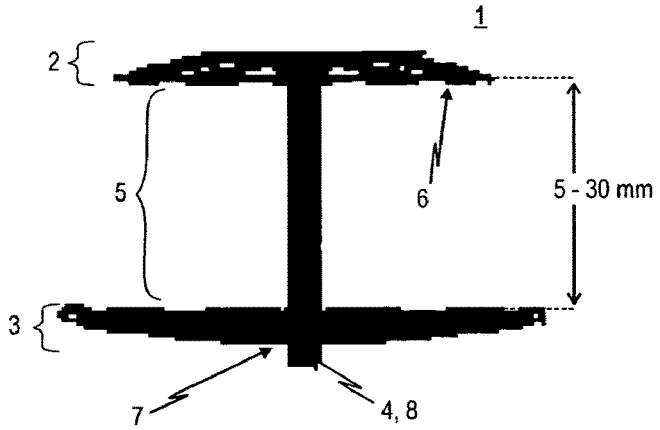
FIG. 1 shows a side view of one embodiment of an occlusion device according to the present invention.
Figure 2:
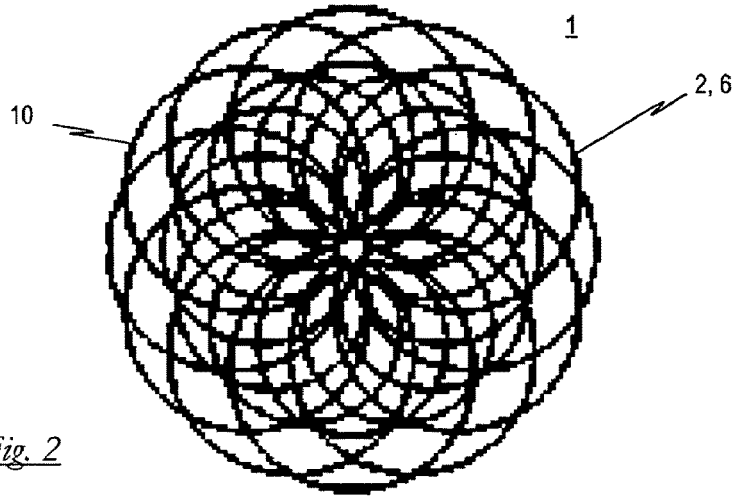
FIG. 2 shows a top plan view of the proximal end of the occlusion device shown in FIG. 1.
Figure 3:
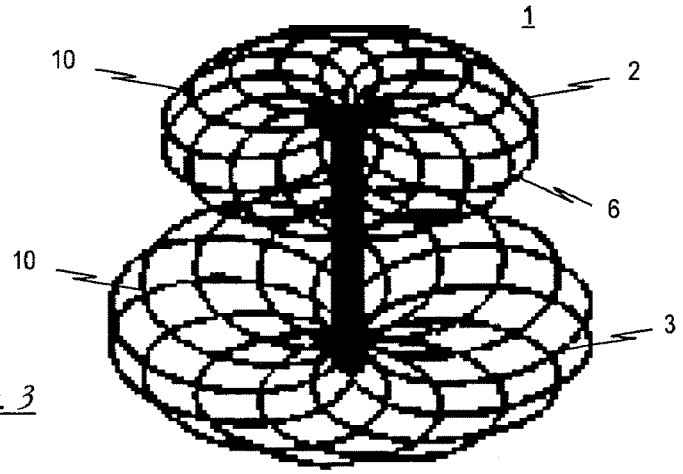
FIG. 3 shows a perspective view of the occlusion device of in FIG. 1.

FIG. 1 shows a side view of a preferred embodiment of the inventive self-expanding occlusion device. FIGS. 2 and 3 show a top plan view of the proximal end and a stereoscopic representation of the embodiment pursuant to FIG. 1.

The inventive occlusion device 1 of the embodiment as depicted includes a braiding 10 of thin wires or threads given a suitable form by means of a molding and heat treatment procedure. The shape to occlusion device 1 depicted in FIGS. 1-3 is that of a barbell-like profile consisting of a front distal retention area 3, a center section 5 and a rear proximal retention area 2. The ends of the wires or threads of braiding 10 converge into a holder 4 in distal retention area 3. In contrast, proximal retention area 2 exhibits a form tapering toward the proximal end.

Proximal retention area 2 is moreover depicted to have a flanged area 6, which is formed by the at least partly folding over of proximal retention area 2 to the distal end.

Braiding 10 is formed from wires or threads which are preferably made from nitinol or other material having shape memory properties or effect. It would also be conceivable here to make use of a polymer synthetic which has shape memory properties, as would be the use of a biologically degradable shape memory material. What is essential is that braiding 10 exhibit enough flexibility so that occlusion device 1 can be tapered to the diameter of a catheter (explicitly not shown) which would be used in a minimally invasive, in particular intravascular, surgical procedure. Because of the material's memory effect, an occlusion device 1 tapered in such fashion exhibits a shape memory function such that subsequent exiting the catheter, the device 1 will expand automatically and re-assume the pre-determined shape corresponding to its application. This usually occurs after the occlusion device 1, initially arranged in the catheter, has been positioned at the site to be treated, in particular in the atrial auricula of a patient's heart.

The pre-determined shape to the occlusion device can also be one not unlike a bell, with the tapering end of the bell-shaped form constituting distal retention area 3. It would also be conceivable for occlusion device 1 to exhibit a mushroom-shaped profile, whereby the cap of the mushroom profile would form the proximal or distal retention area 2, 3. In contrast, the embodiment of the inventive occlusion device depicted in FIGS. 1-3 exhibit—as stated above—a barbell-like shape, whereby the crosspiece of said barbell shape forms the center section 5 between proximal and distal retention areas 2, 3 of occlusion device 1.

Of course, other profile shapes to the occlusion device, however constituted and application-specific, are also conceivable. The barbell-like profile depicted here serves only in the describing of a preferred embodiment of the occlusion device and is in particular not to limit the invention's scope of protection in any way.

In FIGS. 1-3, the inventive occlusion device 1 is shown in its expanded state. As indicated above, occlusion device 1 exhibits a proximal retention area 2, a distal retention area 3 as well as a concave, cylindrical center section 5. Proximal retention area 2 with its configured flanged area 6 primarily serves in the affixing and holding of the implanted and expanded occlusion device 1 in the patient's atrial auricula. To this end, it is provided that flanged area 6 partially positions on the inner walls of the atrial auricula in the atrial auricula to be occluded, realizing a force-fit connection with the inner walls of the atrial auricula; the implanted and expanded occlusion device 1 in thus held in the atrial auricula. It would also be conceivable, for example, for proximal retention area 2 and/or flanged area 6 to be radially pre-stressed so as to ensure a secure hold for the expanded occlusion device 1 given a relatively wide variation of atrial auricula openings.

In implanted and expanded state, distal retention area 3 serves to occlude the atrial auricula as optimally as possible. How the individual retention areas function will be described in greater detail in the following with reference being made to FIG. 4.

The design of inventive occlusion device 1 is based on the principle that occlusion device 1 can be tapered to the size of a catheter. After it exits the catheter, retention areas 2, 3 then unfold by themselves and position against the inner walls of the atrial auricula. Hence, to a certain degree, the inventive design thus entails a self-positioning and self-centering system. Center section 5 thereby has a fixed length pre-defined for the application in order to ensure closing of the atrial auricula opening.

Distal retention area 3 further exhibits a recess 7 in which holder 4 is arranged, into which the ends of the wires or threads of braiding 10 converge. This ensures that in implanted state, no material of the implanted occlusion device 1 can protrude beyond the plane of the atrial auricula into the patient's bloodstream. The provision of such a recess 7 in distal retention area 3 can additionally allow for disposing a connective element 8 at distal retention area 3 without the patient's body mounting any defense mechanism reactions since connective element 8 disposed within recess 7 is effectively prevented from coming into contact with the blood. Connective element 8 can be configured so as to engage with a catheter.

The flexible property to inventive occlusion device 1 afforded by the material used and by braiding 10 allows device 1 to be of a configuration which is reversibly collapsible inward and outward so that an occlusion device 1 already expanded can be re-collapsed, for example by using an explantation catheter, whereby the force-fit joining of flanged area 6 and the inner walls of the atrial auricula can then be disengaged.

Figure 4:
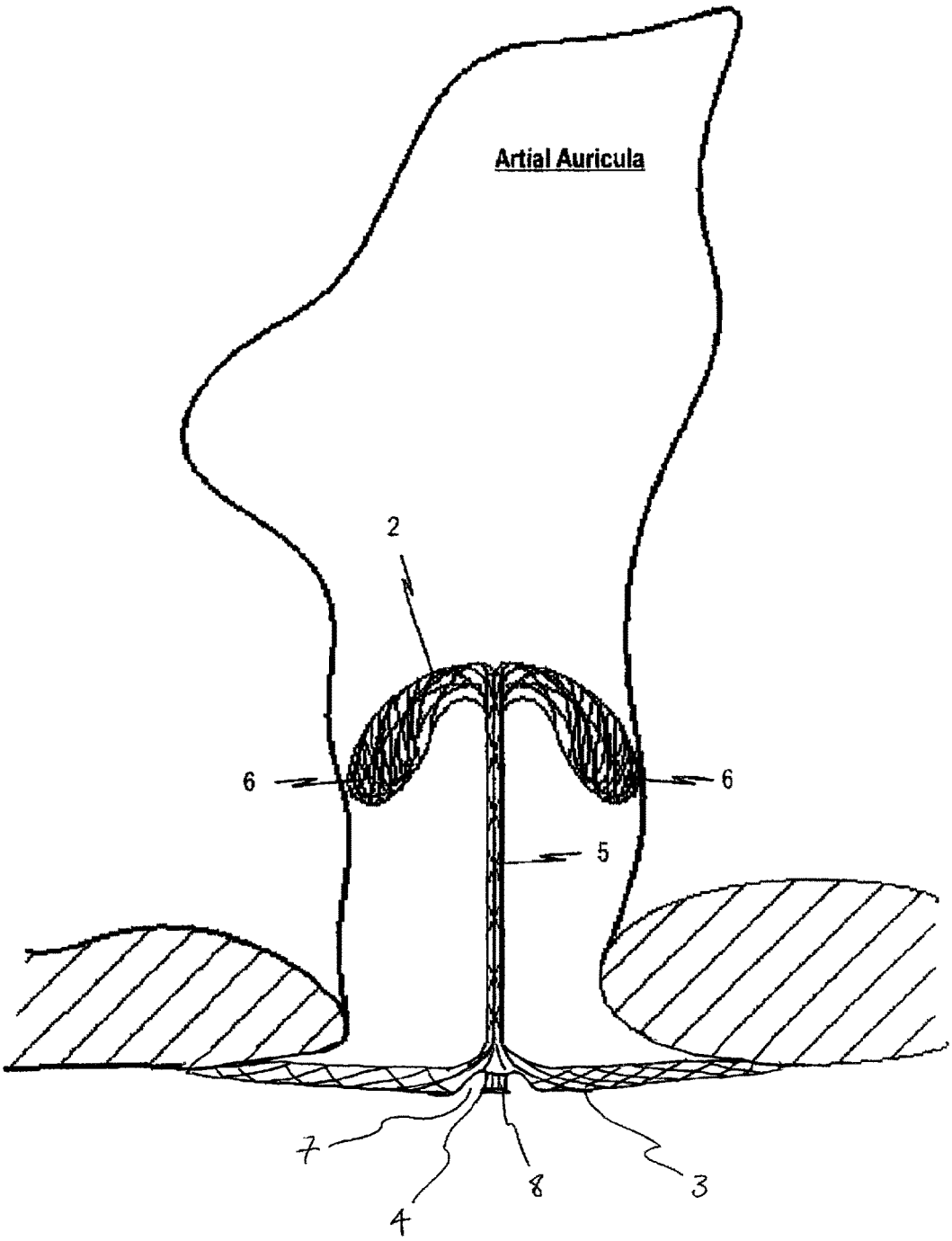
FIG. 4 shows a cross-sectional view of an occlusion device according to certain embodiments of the present invention implanted into the atrial auricula of a patient's left atrium.

FIG. 4 shows the preferred embodiment of inventive occlusion device 1 in implanted state. Specifically, the occlusion device is inserted into the left atrial auricula of the patient's heart and serves to occlude the atrial auricula. In detail, flanged area 6 of proximal retention area 2 abuts the inner walls of the atrial auricula and serves to position and fix the implanted occlusion device 1. In implanted state, distal retention area 3 closes the opening of the atrial auricula, whereby the periphery of the retention area positions against the wall of the atrial auricula opening while center section 5 extends through the opening. The inventive occlusion device 1 thus represents an occluding system which is introduced into the body of a patient and positioned at a specific location for the purpose by means of a minimally invasive procedure; i.e., using a catheter and guidewires, for example. Hereto, distal retention area 3 of device 1 in particular is configured such that no material of implanted occlusion device 1 can extend beyond the atrial auricula wall into the patient's bloodstream. The edge of distal retention area 3 is thereby flush with the atrial auricula wall. This occurs over a relatively wide area independent of the diameter of the atrial auricula or the thickness of the atrial auricula wall at the atrial auricula opening. This thus allows for a complete endothelialization to be realized relatively quickly subsequent implantation of occlusion device 1 and the patient's body will not mount any defense mechanism reactions since the blood is effectively prevented from coming into contact with the material of implant 1.

Although not explicitly depicted in the figures, inventive occlusion device 1 can further-more comprise a fabric insert, same including Dacron material, for example. It would be conceivable here to work fabric inserts into the interior of center section 5 or at the distal end of retention area 3 for the purpose of completely occluding the atrial auricula opening. The inclusion of fabric inserts can ensue, e.g. by bracing same within occlusion device 1. The implant inserted into the body is then completely ingrown by the body's own tissue after just a few weeks or months.

Figure 5:
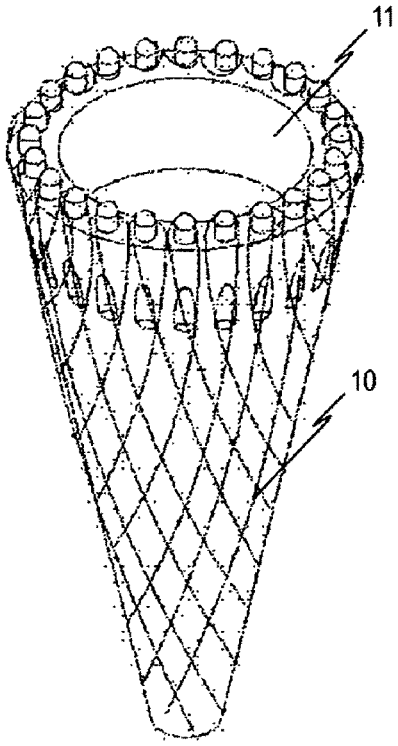
FIG. 5 shows a representative device for producing a wire braiding of which the inventive occlusion device is made.

FIG. 5 depicts a representative device for producing a wire braiding. This round braiding machine 11 is configured such that it forms a funnel-shaped hollow braiding 10 when in operation, whereby the hollow braiding 10 is gathered at a first distal end and remains opens at an opposite second proximal end.

Figure 6:
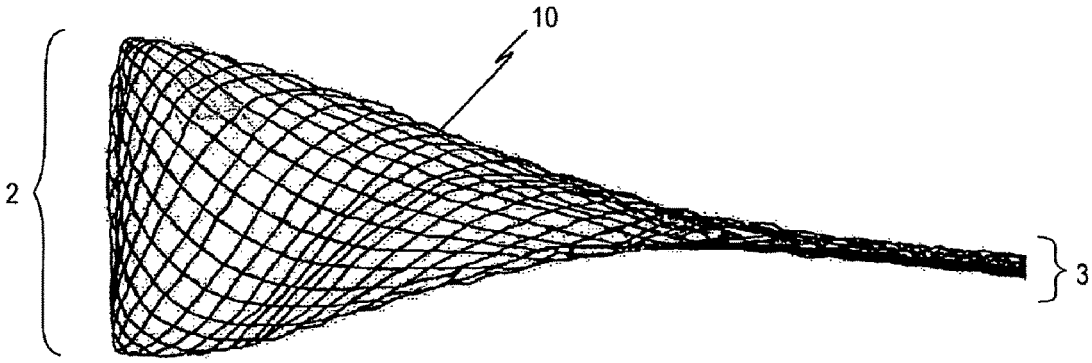
FIG. 6 shows the wire braiding prior to heat treatment (annealing)

FIG. 6 shows a separate representation of the funnel-shaped hollow braiding 10 made with round braiding machine 11. According to this design to the funnel-shaped hollow braiding, proximal retention area 2 at the open second end of braiding 10, distal retention area 3 at the gathered first end of braiding 10, and a center section arranged between said proximal and distal retention areas 2, 3 are formed by means of a heat treatment. Subsequently, a holder 4 is provided at the bundled distal end of funnel-shaped hollow braiding 10. The structuring of the inventive occlusion device's braiding 10 is described in detail in the DE 103 38 702 patent application cited at the outset.

Figure 7:
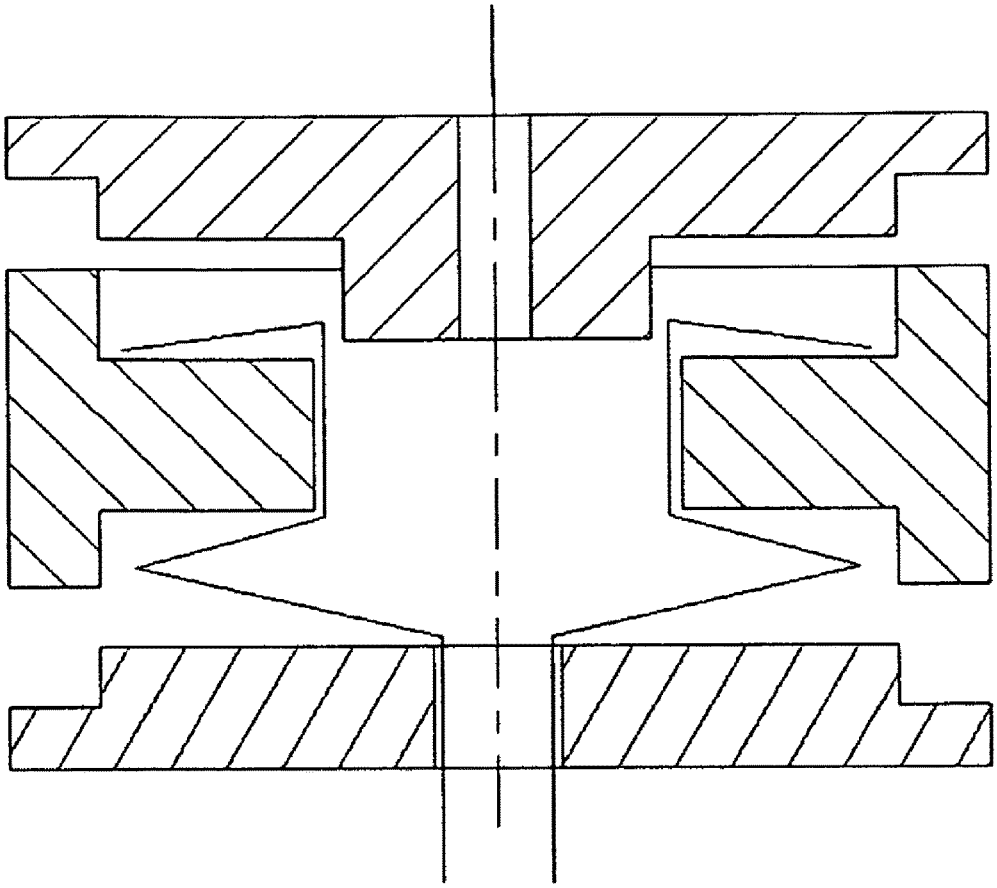
FIG. 7 shows a sectional view of a multi-part device for producing the final form of an inventive occlusion device.

FIG. 7 shows a sectional view of a multi-part device for producing the final form of an inventive occlusion device.

It is emphasized that the realization of the invention is not limited to the embodiments associated with the figures, but rather can be realized in a plurality of variants without departure from the scope of the invention herein involved. It is intended that all matter contained in the above description, as shown in the accompanying drawings, the specification, and the claims shall be interpreted in an illustrative, and not limiting sense.

What is claimed is:

[1. A self-expanding occlusion device comprising:

a braiding of thin wires or threads given a predetermined form by means of a molding and heat treatment procedure, said braiding having:

a proximal retention area comprising a proximal end of the occlusion device that defines an opening to an interior of the occlusion device and a proximal flange biased to deflect towards a distal end of the occlusion device;

a distal retention area comprising the distal end of the occlusion device and a holder in which all ends of the wires or threads converge, the holder positioned interior of the distal end; and a center section disposed between said proximal and said distal retention areas;

wherein the occlusion device can be introduced into the body of the patient in a collapsed state and positioned in a minimally invasive procedure using a catheter.]

[2. The occlusion device in accordance with claim 1, wherein said flanged area of said proximal retention area is configured to deflect towards said distal retention area when said occlusion device is in said expanded state in said target site.]

[3. The occlusion device in accordance with claim 1, wherein said distal retention area exhibits a recess in which said single holder is arranged.]

[4. The occlusion device in accordance with claim 3, wherein at least one connective element is furthermore provided in said recess at said distal retention area, whereby said connective element can engage with a catheter.]

[5. The occlusion device in accordance with claim 1, wherein said occlusion device is configured to be reversibly collapsible so that the expanded occlusion device can be collapsed by means of an explantation catheter.]

[6. The occlusion device in accordance with claim 1, wherein said braiding comprises a polymer.]

[7. The occlusion device in accordance with claim 1, wherein said occlusion device exhibits a mushroom-shaped profile.]

[8. The occlusion device in accordance with claim 1, wherein said occlusion device exhibits a barbell-shaped profile.]

[9. The occlusion device in accordance with claim 1, wherein said braiding collapses to a diameter of a catheter used in a minimally invasive surgical procedure.]

[10. The occlusion device in accordance with claim 1, further comprising a fabric insert.]

[11. The occlusion device in accordance with claim 1, wherein said distal retention area is flush with said opening of said target site when the occlusion device is in said expanded state.]

[12. The occlusion device in accordance with claim 11, wherein an edge of said distal retention area is flush with said opening of said target site when said occlusion device is in said expanded state.]

[13. An occlusion device comprising:

a braiding comprising a plurality of filamentous members having first and second ends;

a proximal retention area comprising a proximal flange that is biased to deflect towards a distal end of the occlusion device and a proximal end of the occlusion device that is open to an interior of the occlusion device;

a distal retention area comprising the distal end of the occlusion device and an outer edge overlapping an opening of a target site when said occlusion device is in a deployed state;

a center section associating said proximal flange and said distal retention area; and a holder bundling said first and second ends of said plurality of filamentous members together, said holder disposed substantially within said distal retention area when said occlusion device is in a deployed state.]

[14. The occlusion device of claim 13 wherein said distal retention area is formed in a shape substantially similar to a shape of an umbrella.]

[15. The occlusion device of claim 13 wherein said holder is disposed in a recess formed at said distal retention area.]

[16. The occlusion device of claim 13 wherein said plurality of filamentous members comprise a shape-memory material.]

[17. The occlusion device of claim 16 wherein said shape-memory material comprises a polymer.]

[18. The occlusion device of claim 13 wherein said holder comprises a connective element.]

[19. The occlusion device of claim 13 wherein said occlusion device is reversibly collapsible to a diameter of a catheter used in a minimally invasive procedure.]

[20. The occlusion device of claim 13 further comprising a fabric insert.]

*21. A self-expanding occlusion device comprising:*

*a structure of thin wires or threads of a shape memory material self-expandable to an expanded shape upon implantation, said structure having:*

*a proximal retention area comprising a proximal flange biased to deflect outward towards a distal end of the occlusion device, the thin wires or threads of the proximal retention area forming at least one opening;*

*a distal retention area forming a distal end of the occlusion device and a recess,*

*a holder in which opposing ends of at least one of the wires or threads of the structure converge, the holder being positioned within said recess; and*

*a center section disposed between said proximal and said distal retention areas;*

*wherein the occlusion device can be introduced into the body of the patient in a collapsed state and positioned in a minimally invasive procedure using a catheter.*

*22. The occlusion device in accordance with claim 21, wherein said distal flange is plate shaped when said occlusion device is in said expanded state in said target site.*

*23. The occlusion device in accordance with claim 21, wherein at least one connective element is provided in said recess at said distal retention area, whereby said connective element engages a catheter.*

*24. The occlusion device according to claim 23, wherein the connective element comprises an internal threading devised to engage with an insertion instrument.*

*25. The occlusion device in accordance with claim 21, wherein said occlusion device is configured to be reversibly collapsible so that the expanded occlusion device can be collapsed by means of an explantation catheter.*

*26. The occlusion device according to claim 21, wherein the distal retention area is configured as a distal umbrella, and the proximal retention area is configured as a proximal umbrella.*

*27. The occlusion device in accordance with claim 21, wherein said occlusion device exhibits a mushroom-shaped profile whereby the cap of the mushroom-shaped profile forms the proximal retention area.*

*28. The occlusion device in accordance with claim 21, wherein said occlusion device exhibits a barbell-shaped profile.*

*29. The occlusion device according to claim 21, wherein the proximal retention area is umbrella shaped, and the distal retention area is plate shaped.*

*30. The occlusion device in accordance with claim 21, wherein said occlusion device is collapsible to a diameter of a catheter used in a minimally invasive surgical procedure.*

*31. The occlusion device in accordance with claim 21, further comprising an insert.*

*32. The occlusion device according to claim 31, wherein the insert is a fabric insert.*

*33. The occlusion device according to claim 31, wherein the insert is arranged in the distal retention area.*

*34. The occlusion device according to claim 33, wherein the insert is stretched over at least a portion of the structure.*

*35. The occlusion device according to claim 31, wherein the holder comprises an internal threading devised to engage with an insertion instrument.*

*36. The occlusion device in accordance with claim 21, further comprising a tractive force exerted across the center section by the proximal retention area configured to hold the distal retention area at the opening of said target site, whereby said distal retention area is configured to be flush with said opening of said target site when the occlusion device is in said expanded state.*

*37. The occlusion device in accordance with claim 36, wherein an edge of said distal retention area is configured to be flush with said opening of said target site when said occlusion device is in said expanded state.*

*38. The occlusion device in accordance with claim 21, wherein at least a portion of the structure comprises a braiding of the thin wires or threads.*

*39. An occlusion device comprising:*

*a plurality of shape-memory filamentous members;*

*a self-expanding proximal retention area comprising a flange biased to deflect towards a distal end of the occlusion device and at least one opening therethrough;*

*a self-expanding distal area comprising an outer edge configured to overlap an opening of a target site when said occlusion device is in a deployed state;*

*a center section associating said proximal flange and said distal area; and*

*a holder bundling opposing ends of at least one of said plurality of filamentous members together, said holder disposed substantially proximal of a distal end of said occlusion device when said occlusion device is in a deployed state.*

*40. The occlusion device of claim 39, wherein said distal area is formed in a shape substantially similar to a shape of an umbrella.*

*41. The occlusion device according to claim 39, wherein the proximal flange is formed in a shape substantially similar to a shape of an umbrella.*

*42. The occlusion device of claim 39, wherein said holder is disposed in a recess formed at said distal area.*

*43. The occlusion device of claim 39, wherein said plurality of filamentous members comprise a metallic shape-memory material.*

*44. The occlusion device of claim 43, wherein said plurality of filamentous members comprise a polymeric shape-memory material.*

*45. The occlusion device of claim 39, wherein said holder comprises a connective element.*

*46. The occlusion device according to claim 45, wherein the connective element comprises an internal threading devised to engage with an insertion instrument.*

*47. The occlusion device of claim 39, wherein said occlusion device is reversibly collapsible to a diameter of a catheter used in a minimally invasive procedure.*

*48. The occlusion device of claim 39, further comprising an insert.*

*49. The occlusion device of claim 48, wherein the insert is a fabric insert.*

*50. The occlusion device of claim 48, wherein the insert is arranged in the distal area.*

*51. The occlusion device of claim 50, wherein the insert is stretched over at least a portion of the occlusion device.*

*52. The occlusion device of claim 39, further comprising a tractive force exerted across the center section by the proximal flange configured to hold the distal area at the opening of said target site, whereby said distal area is configured to be flush with said opening of said target site when the occlusion device is in said deployed state.*

*53. The occlusion device of claim 39, wherein said proximal flange is configured to deflect towards said distal area when said occlusion device is in said deployed state.*

*54. The occlusion device in accordance with claim 39, wherein at least a portion of the occlusion device comprises a braiding of the plurality of shape-memory filamentous members.*

*55. An occlusion device comprising:*

*a plurality of shape-memory wires or threads;*

*a self-expanding proximal area having an opening formed therethrough and a flange folded towards a distal end of the occlusion device to form an open umbrella-like profile;*

*a self-expanding distal area having an outer edge configured to overlap an opening of a target site when said occlusion device is in a deployed state and a connective element that reversibly engages an insertion instrument, the connective element at least partially recessed from the distal end of the occlusion device when the occlusion device is in a deployed state and binding opposing ends of at least one of the plurality of shape-memory wires or threads; and*

*a central portion connecting the proximal area to the distal area.*

*56. The occlusion device of claim 55, wherein the connective element is provided in a recess formed in the distal area.*

*57. The occlusion device of claim 55, wherein at least a portion of the plurality of shape-memory wires or threads are braided.*

*58. The occlusion device of claim 55, wherein the distal area has an umbrella-like profile.*

*59. The occlusion device of claim 55, wherein the proximal area, central portion, and distal area form a barbell-shaped profile.*

*60. The occlusion device of claim 55, wherein the distal area has a plate-like profile.*

*61. The occlusion device of claim 55, wherein the self-expanding proximal area, central portion, and distal area are reversibly collapsible from an expanded deployed state to a collapsed state.*

*62. The occlusion device of claim 55, wherein the distal area comprises an insert.*

* * * * *